United States Patent [19]

Forssmann et al.

[11] Patent Number: 4,936,291
[45] Date of Patent: Jun. 26, 1990

[54] CONCREMENT LOCATING APPARATUS UTILIZING X-RAYS AND ULTRASONIC DETECTORS

[75] Inventors: Bernd Forssmann, Friedrichshafen; Hans-Heinrich Gerth, Meersburg; Othmar Wess, Immenstaad, all of Fed. Rep. of Germany

[73] Assignee: Dornier System GmbH, Friedrichshafen, Fed. Rep. of Germany

[21] Appl. No.: 753,658

[22] Filed: Jul. 10, 1985

[30] Foreign Application Priority Data

Jul. 18, 1984 [DE] Fed. Rep. of Germany ....... 3426398

[51] Int. Cl.$^5$ ............................................. A61B 6/00
[52] U.S. Cl. ............................. 128/660.03; 606/128
[58] Field of Search .................. 128/24 AL, 328, 630, 128/1 R, 660.03, 24 AA; 606/128

[56] References Cited

U.S. PATENT DOCUMENTS 3,893,449 7/1975 Lee et al. ........................... 128/24 A
4,315,514 2/1982 Drewes ............................. 128/24 A
4,610,249 9/1986 Makofski et al. .................. 128/328

FOREIGN PATENT DOCUMENTS 3037471 5/1982 Fed. Rep. of Germany ....... 128/630

OTHER PUBLICATIONS

Shock Wave Treatment for Stones in Upper Urinary Tract by Christian chaussy Nov. 1983.
*Extracorporeal Shock Wave Lithotripsy*, Chaussey et al., Pub. S Karger A.G., Basel, Switzerland, 1982.

*Primary Examiner*—Leonard E. Smith
*Attorney, Agent, or Firm*—Ralf H. Siegemund

[57] ABSTRACT

The present invention relates to the locating of concrements in the body of living beings for the purposes of determining where the focal point of a shock wave reflector has to be positioned so that it may comminute the concrement, and more particularly the invention relates to a system for locating concrements under utilization of X-rays in combination with an ultrasonic device.

5 Claims, 2 Drawing Sheets

CONCREMENT LOCATING APPARATUS UTILIZING X-RAYS AND ULTRASONIC DETECTORS

BACKGROUND OF THE INVENTION

The present invention relates to the locating of concrements in the body of living beings for purposes of determining where the focal point of a shock wave reflector right has to be positioned so that it may comminute the concrement, and more particularly the invention relates to a system for locating concrements under utilization of X-rays in combination with an ultrasonic device.

German patent No. 23 512 47, see also U.S. pat. No. 3,942,531, discloses a device for the comminution of concrements inside the body of a living being, under utilization of a focusing chamber which is a portion of a rotational ellipsoid, having two focal points. In one focal point a spark discharge produces a highly concentrated point like shock wave which propagates in all directions, is reflected by the focusing chamber and refocused in the second focal point of this ellipsoid. That second point must be positioned such that it coincides with the concrement. The comminution of kidney stones without operative invasion and without introduction of probes or the like into the body has been successfully practiced with this technique. An extensive description of equipment and therapeutic procedure is for example found in "Extra corporal shock wave lithotripsy", Ch. Chaussy ed Munich 1982.

Before this shock wave comminution process can take place, it is necessary to very accurately determine the location of, for example, the kidney stone, so that the focusing chamber can be positioned for purposes of having its second focal point as defined above coincide with the kidney stone. For this one has used for example two X-ray systems, which operate basically, on the principle of triangulation and are oriented to obtain particular axes of observation that will pass through the concrement and from the orientation of the X-ray system and their respective axes one can then determine the location of the kidney stone vis-a-vis the X-ray system. The focusing chamber is then positioned accordingly.

Obviously intensive exposure of the patient to X-rays have to be avoided so that the number of X-ray images taken should be limited Nevertheless, the known locating method is tied to two X-ray systems. Following the locating of the kidney stone which in turn is followed by positioning of the focusing chamber, the kidney stone is comminuted by the shock waves to obtain a very fine grit, which is discharged from the body by natural process.

The German patent No. 27 22 252, suggests a device for locating concrements by means of ultrasonics. Satisfactory results for this approach presupposes that the stone and the organs around it have a fixed, resting position. However certain inherent motion of the stone and of the organ in which the stone is lodged, for example on account of breathing will cause the stone to move in and out of the plane of ultrasonic locating. Therefore, the ultrasonic image will change continuously and the stone can be identified only for a very short period of time, namely when it passes through the locating plane to which the ultrasonic imaging system adjusted.

As the focusing chamber is positioned so that its second focal point as mentioned above, is made to coincide with a point in the imaging plane, super imposed oscillatory motion of the stone, may in fact destroy the locational information about the position of the stone and the entire locating procedure may have to be repeated. This process is particularly time consuming if the positioning of the concrement, for example by shifting the patient in relation to a particularly adjusted and positioned focusing chamber is carried out independently from the concrement locating device, i.e. if there is no follow-up control involved. A more suitable tracking device is suggested by one of us and others of copending patent application now issued as U.S. Pat. No. 4,669,483.

DESCRIPTION OF THE INVENTION

It is an object of the present invention to provide a new and improved method and equipment for locating concrements in a body of a living being, in preparation of a comminution process using focused shock waves whereby the locating of the concrement should be carried with certainty so that the concrement can be placed with certainty and in a simple fast and reliable manner into the one focal point of the reflector and maintaining that adjusted position.

In accordance with the preferred embodiment of the invention it is suggested to use two imaging systems for locating a concrement one being an X-ray system, and the other one an ultrasonic imaging equipment and to correlate the images such that a common dimension appears on the imaging screens, or can be made by way of adjustment to so appear. Preferably the adjustment is made such that any oscillatory movement of the concrement occurs in one line or one image and in the display plane (screen) of the other image. Generally speaking each image screen should have visible at least one reference point or points. In the example explained with reference to the drawings, the center of the X-ray screen and the center on the ultrasonic screens are such reference points.

The inventive correlation of the two different locating systems two imaging screens permit the rapid detection of a concrement at a higher degree of certainty with regard to recognition, as well as simple observation of the displacement excursions the concrement undertakes on account of breathing by the patient. The correlation of the two locating systems in relation to the positioning permits in fact a rapid follow-up and tracking of the concrement so as to maintain it in the focal area of the shock wave generator. The follow-up may be carried out by the operating personnel or automatically through automated image processing, for example under utilization of an interactive screen system. The utilization of at least one ultrasonic locating system permits in particular the monitoring of the movement of the concrement in real time and without any undue radiation load. The shock waves can always be triggered whenever the stone does in fact pass through the focus on account of the breathing by the patient, which imparts the displacing oscillatory motion upon the stone. Obviously, this increases the efficiency of the comminution and is beneficial for the patient, also the total treatment time is shorter and the use life of the sparking equipment is extended.

The combination of an ultrasonic system with an X-ray system in accordance with the invention, combines the advantages of ultrasonics, namely no damage to the patient, with advantages of X-ray's high resolution. The combination actually is quite ideal, particularly in view of kidney stone comminution but also gall stone comminution. In the case of a kidney stone comminution, the advantages of X-ray become noticeable, particularly upon evaluation the sequence of treatment and its success and while the ultrasonic approach is used only for determining the depth and position of the concrement.

In the case of gall stone comminution however, X-rays are used primarily for preorienting and to generally find the position of a stone in order to find an optimum section plane, so that now the advantages of ultrasonic can be used to the fullest. It is possible for example to use the X-ray system as an aid in the orientation of the ultrasonic locating system, B scan. A single X-ray system generally will find only two out of three spatial coordinates of the target. The X-ray image plane and the ultrasonic image plane are preferably arranged at right angles to each other to thereby determine the missing third coordinate of the X-ray from the ultrasonic image.

Both systems moreover are arranged such that they establish a representation for the second focal point of the ellipsoid (the first one is the one, in which the spark is produced). In cases with insufficient certainty about concrement recognition, one can use the X-ray locating procedure for controlling the two out of three coordinates which of course increases the certainty of recognition, or it is used primarily for preadjusting the concrement in two dimensions and permits thereafter a simpler and faster recognition of the third coordinate under utilization of the ultrasonic system, to thereby determine this third coordinate for purposes of positioning the focusing device.

Any periodic movements of the concrement, primarily induced by breathing, can be observed in real time on the ultrasonic image. For better tracing of such periodic movements one should provide the ultrasonic system such that it can turn about an axis which runs through the center of the ultrasonic oscillator itself as well as the focal point F2, this is also called a Uo axis. As soon as the positioning is carried out in the stated manner, a simple axial turning of the ultrasonic oscillator under observation of the ultrasonic image permits orienting the ultrasonic image plane parallel to the main axis and direction of oscillation of this particularly moving target. This way one can operate without complex variable coordinate transformation and still obtain a reliable target acquisition in real time.

In a particular embodiment of practicing the invention, it is conceivable to provide the ultrasonic system so as to rotate the detection plane about two axes. Each rotation and rotational adjustment permits separate adjustment such that the oscillation occurs within the plane. The oscillator can thus be observed from different angles. In each case therefore the stone is permanently on the ultrasonic image screen.

To have these two different situations available is representable by different images for each of these two different rotations. The advantage here is that in fact the stone becomes visible from different sides, and its volume can therefore be calculated by means of an online calculator, which is important information concerning accurate metering the shock wave energy to be produced.

In a particular embodiment of the invention it is suggested to correlate the positioning of the shockwave generator with the two locating systems. This, for example, is obtained in that two coordinate directions are caused to coincide with the ultrasonic imaging and detection plane and the third coordinate is then at least approximately perpendicularly thereto. By moving the patient in the direction of that third coordinate, the target, i.e. the concrement will appear or disappear within the ultrasonic image field, and with the aid of the two coordinates being visible as such in the imaging plane of the ultrasonic monitoring screen, the particular location of the concrement in that plane can easily be ascertained. Since now only correction in the direction of these two image field coordinates are necessary, the target is continuously visible and will not move out of the field of view accidentally. This means that the locating process is quite a speedy one. The locating procedure can be carried out considerably faster and in real time and particularly larger correction can be provided in coarse step for example through push button advance still remaining fully under control, either by an operator or by automated equipment.

The shifting of the ultrasonic section plane may be automated, also, under utilization of a computer. Evaluation in this case, may for example be carried out through an interactive imaging screen, using for example a light pen, the attending physician uses to point to the location of the stone, and the positioning equipment will then automatically move for example the patient or the patient rest so that the stone appears in the center of the image screen with oscillations occurring within the imaging plane of the ultrasonic equipment. Alternatively the initial location of the stone on the screen can be read through proper scales and these coordinate values are then keyed into the calculator.

The most important aspect is that the invention reliably prevents that the target appearing in the ultrasonic image screen will in fact escape so that another time consuming search process has to begin. This mishap does occur in uncorrelated system. The danger of unintended escape of the target (concrement) from the screen in previous locating equipments was specifically due to the fact that the ultrasonic image so to speak depicts only a thin slice from the object field, and that a representation of the target is possible only if the target is in some form correctly placed within the coordinate system that is inherit in the ultrasonic system. In the case the coordinate system for the patient positioning and the coordinate system for the ultrasonic imaging are rotated in relation to each other any position correction may cause the image of the concrement to move in the sense that if a correction that is carried out in one coordinate system may lead to an escape of the image from an ascertained position in the other coordinate system.

Generally speaking one uses two imaging systems with image planes that are oriented perpendicular to each other. In furtherance of the invention one may use two ultrasonic systems. This is advantageous if one wishes to track the concrement movement fully through automated follow-up control and this can be carried out in fact in real time. In this case, the located concrement will appear in both ultrasonic images, which means that two out of three coordinate systems are in fact represented in each of the ultrasonic systems. For example X and Y appear in system 1, Y and Z in system 2. From the real time ultrasonic images now all requisite corrections are directly ascertainable to provide follow-up control input signal in real time whereby for example the direction of movement n three coordinates, the speed and the acceleration are sufficiently fast detected to permit tracking of the relatively slowly moving concrement. Servo motors provide in effect correction of the concrement position, so that the concrement is in fact maintained in the second focus of the shock wave focusing and generating device. The ascertaining of corrective data in respective two coordinates such as X, Y in system 1, can be carried out in different ways, for example by means of image storage facilities; correlation techniques, or by means of an automatic symbol recognition device or through application of separate position 1 for each ultrasonic system. This last 1 possibility is particularly simple, because such position detectors are commercially available, and a movement of a defined image point in two dimension can be acquired by these position detectors as to direction, speed and acceleration. In connection with two ultrasonic systems then one has therefore available all the requisite data for correction. Finally it should be mentioned that a real time position correction is possible for kidney stone comminution, as well as for gall stone comminution.

DESCRIPTION OF THE DRAWINGS

While the specification concludes with claims, particularly pointing out and 2 claiming the subject matter which is regarded as the invention, it is believed that the invention, the objects and features of the invention, and further objects, features and advantages thereof, will be better understood from the following description taken in connection with the accompanying drawings in which:

Proceeding now to the detailed description of the drawings, FIG. 1 illustrates somewhat 2 and in cross section the body 2 of a patient and reference numeral 4 denotes a concrement to be comminuted. Also schematically shown is a shock wave reflector 6, of the type mentioned above, having a first focal point F1, in which is situated the source of shock waves. In other words spark discharges are produced in the focal point F1, and are reflected and refocused by the reflector 6 in the second focal point F2. The ultimate objective is the preparation phase for making the concrement 4 coincide with that second focal point F2. Not shown in the drawings are devices for relatively shifting and positioning the patient body 2 vis-a-vis the reflector 6, it does not make any difference in principle which (or who) is being moved, but for practical purposes, one usually has the equipment 6 fixed and the body 2 is situated on a suitable rest and the rest as a whole or portions of the rest are being shifted for positioning the patient body in particular relation to the reflector 6. The movement can be carried out manually. Also not shown are structure for coupling and/or introducing the shock wave energy into the body. Generally speaking it is advisable to have the focal chamber filled with liquids, such as water and to provide in some form a water coupling path between the device 6 and the body of the patient.

Figure 1:
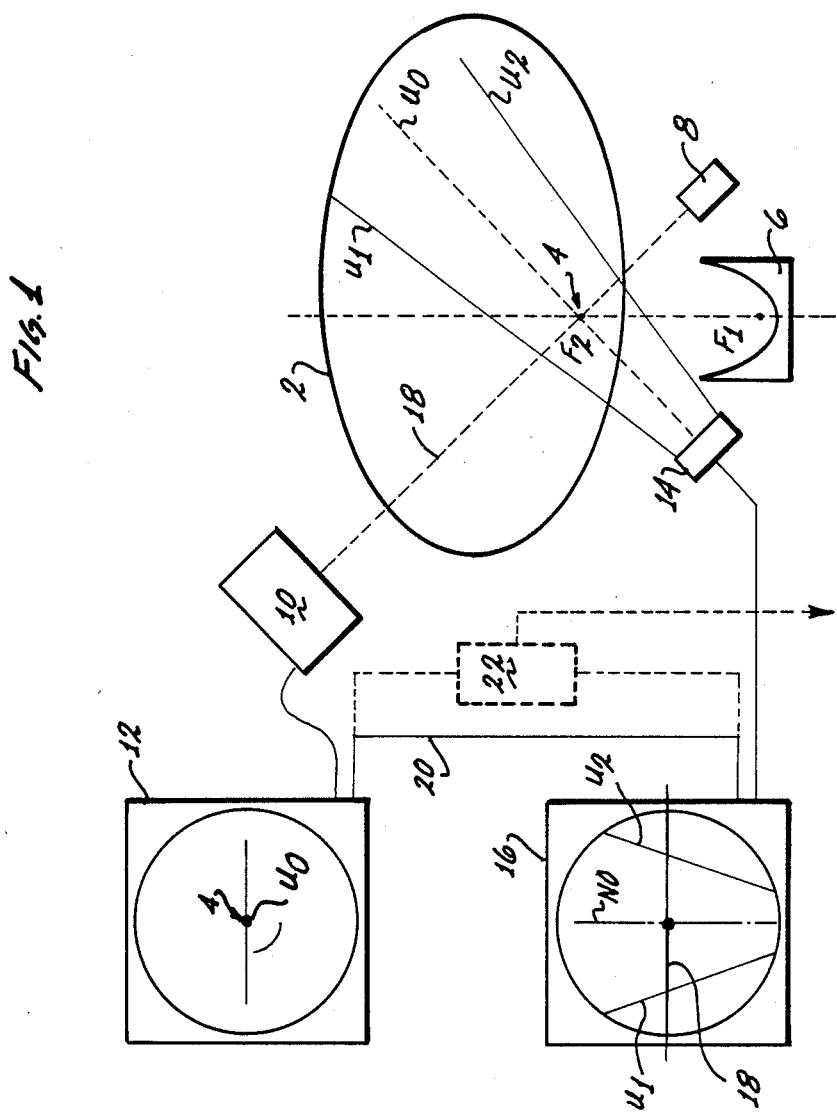
FIG. 1 is a somewhat schematic view of a system in accordance with the preferred embodiment of the present invention for practicing the best mode thereof.

The inventive locating system is comprised of an X-ray locating system including an X-ray tube 8 and an X-ray image receiver and amplifier 10, being connected to an X-ray image monitor 12. The second locating system is an ultrasonic system comprised of an ultrasonic transducer, i.e. emitter/receiver head 14, being connected to an ultrasonic imaging monitor and screen 16, responding to the return and reflection of ultrasonic waves.

The correlation between the two monitors and indicators 12 and 16 is denoted symbolically by the connection 20 and correlation can be automated, but does not have to; the operative correlation can be provided by an attending physician or technician. Decisive for the invention are the facilities that permit correlation. FIG. 1 also contains in superimposed relationship an alternative configuration using a correlation computer or calculator 22, the output of which runs to adjusting motors for the positioning device of the patient and his other rest as was outlined above. The correlative procedure can thus be automated. In case one uses a calculator 22, the coordinates are determined through a scanning process of the two screens 12 and 16 i.e. of its information content. Thus scanning may be a purely electrical one, involving amplitude proceedings of the signals that are used to control and determine the respective images.

In case of an error for example, it can be calculated whether or not the positioning data are compatible, because two coordinate of the ultrasonic system and two coordinates of the X-ray system together are redundant for determining the three coordinates of the concrements. Therefore it is quite possible to calculate whether or not the coordinate values as provided in each of the two scanning systems are compatible with the respective other one.

As far as the locating and positioning procedures are concerned, the ultimate objective can be defined as follows: The reflector (6) axis is defined by a line through the two focal points F1 and F2, the center line 18 of the X-ray beam and the center line U O of the ultrasonic intersection plane bounded by U1 and U2 are supposed to intersect right in focal point F2. However, all these three axes do not have to be situated in a common plane; it is merely required that they intersect and, of course, the concrement 4 has to be right in that point of intersection.

The ultrasonic sensor 14 being for example of the sector scan variety, or having as a pick-up an array of ultrasonic transducers is provided to obtain a two-dimensional image, generally known from medical diagnostics as a B-scan. The ultrasonic system produces a range image by processing and evaluating transit time of individual beams and transit time differences. For this, a particular locating or section plane is scanned being in effect limited by the beam U1 and U2. The screen 16 in FIG. 1 illustrates schematically the scanned plane as bounded by U1 and U2. The axis Uo runs centrally in that plane. The screen 16 illustrates somewhat schematically this particular scanning plane portion bounded by U1 and U2, therefore what is imaged on the screen is a top elevation, which in this case, is assumed to hold the concrement or stone 4.

The ultrasonic system is particularly adjusted such that the central beam 18, of the X-ray system runs in that plane, bounded otherwise by U1 and U2. The center beam 18 of the X ray system is of course adjusted to coincide with and run through the located concrement. This is particularly illustrated in the screen picture of screen 12. One can also say that the search for a concrement begins by this X-ray locating operation and the first 4 in the composite locating and adjusting and positioning procedure is to center the X-ray equipment vis-a-vis the patient such that the concrement 4 appears in the middle of the screen 12. There may be a suitable cross on the screen for obtaining manually this adjustment. The screens 12 and 16 show the image correlation of concrement 4; it just be on the center of either screen. This establishes the relative position of the two locating systems. The focusing and shock wave producing device 6 must now be positioned that its focal point F2 coincides with the adjustment center of the imaging devices which coincide with the concrement. Procedure is explained in the above identified copending application. From a different point of view, one can see that each of the video screens depict a two dimensional representation. This means that one dimension is redundant and this fact is used for purposes of correlating the two images (or the video signal, representing these images. In FIG. 1 (and the others) the common dimension runs along line U o.

The ultrasonic transducer head 14 should be arranged to avoid damage from the shock wave generator, therefore the head 14 should be placed, so to speak, in the shadow of the reflector and shock wave generator 6. The ultrasonic equipment is now adjusted so that likewise the concrement image appears in the center of monitor screen 16. The ultrasonic imaging plane is superimposed in sections on the X-ray monitor screen 12.

Figure 2:
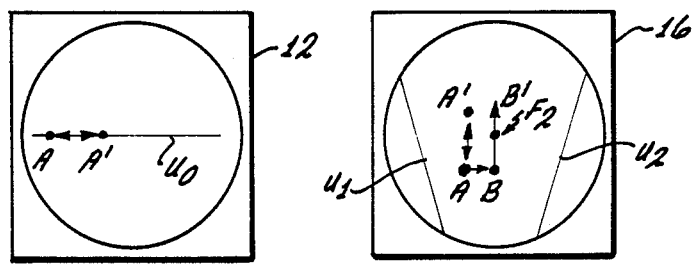
FIGS. 2, 3 and 4 are different X-ray and ultrasonic images for respective three different situations as they arise during locating and positioning of a concrement that moves in the body of a living being on account of breathing.
Figure 3:
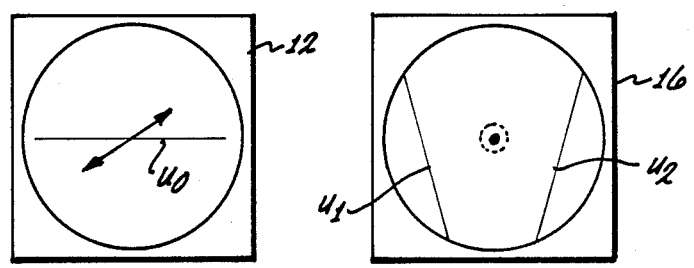
Figure 4:
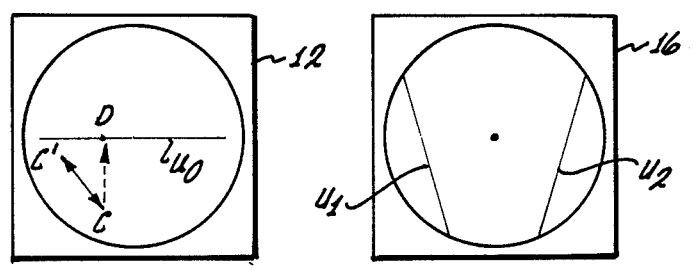

FIGS. 2, 3 and 4 illustrate three different situations of locating a concrement. FIG. 2 is basically similar to the situation, used as a representation for images in FIG. 1, except that it is now assumed that the concrement moves on account of breathing which movement will occur visible on the X-ray screen 12, as well as on the ultrasonic screen 16. The concrement 4 in particular moves back and forth within the plane bounded by lines U1, U2 from position A to position A' and back. It is assumed moreover, that a translatory movement can be provided to move the stone from A to B. This would mean that its oscillatory motion from B to B' runs through the focal point F2. In order to avoid undue X-ray load, the movement of the image of the concrement can be observed by the ultrasonic equipment. The image of the concrement will remain visible on the X-ray screen, but that is redundant so that the X-ray equipment can be switched off.

In FIG. 3, the lefthand portion illustrates that the concrement oscillates on account of breathing through the focal point but the excursions runs between positions above and below the ultrasonic detection plane. In the ultrasonic image as per screen 16, one will simply see briefly the stone image appear and disappear again. The X-ray equipment will show these excursions, but the objective is to reduce X-ray exposure time.

If now the ultrasonic head 14 is rotated about the axis Uo and by the angle visible initially on the X-ray screen 12, one will now cause the concrement to oscillate within the ultrasonic detection plane which is beneficial twofold. Once the oscillation of the concrement in the X-ray screen does no longer move at an angle to the ultrasonic section and detection plane, but its movement coincides therewith, the ultrasonic image of the conrement will not longer appear and disappear on screen 16, but remain permanently visible and oscillates just analogous to the situation shown in FIG. 2. As stated this redundancy of detection is not necessary, which means that the X-ray equipment can be turned off, in order to remove the X-ray load from the patient, one simply has to observe the appearance and disappearance of the ultrasonic image of the concrement Q on the ultrasonic screen 16. Upon rotating the ultrasonic plane, the concrement should permanently appear visible on screen 16 in one adjusting position of ultrasonic section plane rotation and once this has been achieved, the locating procedure is completed. Conceivable a lateral translatory motion has to be provided in addition which is analogous to the situation explained with reference to FIG. 2. In other words FIG. 3 and 2 represent sequential operations in some case.

The example shown in FIG. 4, it can be regarded as the general case, which means that initially the stone is not visible at all on the ultrasonic image screen. The X-ray screen shows that the stone oscillates between positions C and C' both outside and on one side of the ultrasonic detection and section plane. The patient will now be moved translatorily until the stone oscillates through the ultrasonic plane, which occurs by shifting from C to D. This then establishes the situation explained above with reference to FIG. 3. After rotating the ultrasonic image plane and after another translatory shift (FIG. 2) the oscillation passes through the focal point F2.

It should be noted that the ultrasonic plane is either rotated about the axis 18 or analogously to FIG. 3, about the axis Uo. Until the oscillation occurs fully in the ultrasonic plane. Further procedure is thus carried out just as described earlier with reference to the other figures. It should be noted, that this explanation given here of the adjustment operations can be carried out manually but in view of the particular definitiveness of image representation, automatic video signal scanning can be employed, in other words the oscillatory motion and the particular location of that motion of the concrement can readily be acquired through a data process input structure, so that objective data are available, which in turn permit the patient to be automatically positioned until the desired situation, as depicted in FIG. 1 is maintained.

The invention is not limited to the embodiments described above, but all changes and modifications thereof, not constituting departures from the spirit and scope of the invention, are intended to be included.

We claim:

1. In an apparatus for non-invasive comminution of concrements in living beings by means of a shock wave source and a reflector reconcentrating shock waves into a focal point, the improvement for locating and tracking the concrement in relation to said focal point, comprising:
    two locating systems one being an ultrasonic system, the other one being an X-ray system;
    means for correlating the two locating systems such that in each of the imaging systems a reference point representing a center beam of the respective other system is introduced to become visually ascertainable, and to render visible the imaging plane of the respective other system, the two object planes being oriented at right angles to each other; and
    means for providing a visual representation of said focal point in each of the two imaging systems.

2. Apparatus as in claim 1, said ultrasonic system being rotatable about its center axis.

3. Apparatus as in claim 1, said ultrasonic system being rotatable about a center axis of the X-ray system.

4. Apparatus as in claim 1, said ultrasonic system being rotatable about an axis of rotational symmetry of said reflector running through said focal point.

5. Apparatus as in claim 1, wherein the center beam of the X-ray system is oriented to run in an ultrasonic locating plane as defined by the ultrasonic system, a representation of said locating plane being introduced to be visible in the imaging system of the X-ray system.

* * * * *